United States Patent [19]

Ehrlich

[11] 4,221,221
[45] Sep. 9, 1980

[54] UTILITY DIAPER STRUCTURE

[76] Inventor: Jimmie L. Ehrlich, Rte. 2, Wilson, Kans. 67490

[21] Appl. No.: 907,831

[22] Filed: May 19, 1978

[51] Int. Cl.³ ...................... A61F 13/16; A61F 13/18; A61F 13/20
[52] U.S. Cl. .................................. 128/284; 128/287; 206/581
[58] Field of Search ............... 206/229, 210, 216, 581; 132/79, 83 R, 88.5, 88.7; 128/284, 287, 295

[56] References Cited

U.S. PATENT DOCUMENTS

| | | | |
|---|---|---|---|
| 2,066,946 | 1/1937 | Reiman | 206/440 |
| 2,102,858 | 12/1937 | Schlumbohm | 206/823 |
| 2,637,439 | 5/1953 | Banks | 206/823 |
| 2,834,459 | 5/1958 | Rickard et al. | 206/440 |
| 2,940,449 | 6/1960 | Thomson | 206/440 |
| 2,952,354 | 9/1960 | Whitelaw et al. | 206/440 |
| 3,017,990 | 1/1962 | Sigerman | 206/440 |
| 3,534,887 | 10/1970 | Ginsberg | 206/812 |
| 3,561,456 | 2/1971 | Stuart, Jr. | 206/812 |
| 3,565,075 | 2/1971 | Jerry | 128/260 |
| 3,635,567 | 1/1972 | Richardson, Jr. | 206/812 |

*Primary Examiner*—William E. Kamm
*Assistant Examiner*—C. W. Shedd
*Attorney, Agent, or Firm*—Phillip A. Rein

[57] ABSTRACT

This invention relates to a utility diaper structure having a plurality of container assemblies connected to a diaper assembly. The diaper assembly resembles a conventional type, size, and shape having a main body member with a connector assembly to aid in connection of upper edges thereof. The container assemblies are a plurality of sealed members, each of which are releasably connected to the main body member. More specifically, the container assemblies are (1) a powder packet assembly having a baby powder material sealed within a container member; (2) a towel packet assembly having a towel member sealed within a container member; and (3) a baby oil packet assembly having a baby oil material sealed within a container member.

9 Claims, 4 Drawing Figures

UTILITY DIAPER STRUCTURE

PRIOR ART

A search of the prior art structures revealed the following patents:

U.S. Pat. Nos. 2,544,840, 3,137,862 and 1,995,531.

The Mizerak patent discloses shorts with a concealed money pocket. The Kowatsch patent discloses a bathing trunk with a waterproof pocket.

The Bachelis patent discloses swimming trunks with side zippers.

It is noted that none of the patents disclose a diaper structure having sealed, removable packets containing materials therein that are essential to the care of a human baby.

SPECIAL EMBODIMENT OF THE INVENTION

In one preferred embodiment of the invention, a utility diaper structure is provided including a diaper assembly having container assemblies connected thereto. The diaper structure includes a main body member having a connector assembly secured thereto. The main body member resembles a reusable type or a disposable type diaper of conventional size and shape. The connector assembly includes left and right tab members which can be connected by snap members or pin members to a portion of the main body member when in the usage position. The container assemblies are a plurality of sealed members, each being releasably connected to the main body member. The container assemblies include (1) a powder packet assembly; (2) a towel packet assembly; and (3) a baby oil packet assembly. Each of the aforementioned packet assemblies include a sealed container member, each having a respective one of a powder material; a towel member, or a baby oil material therein. It is noted that the baby care elements can be used and then disposed of with the respective container members with the remaining diaper assembly utilized in a conventional manner.

OBJECTS OF THE INVENTION

One object of this invention is to provide a utility diaper structure having a removable container assembly thereon to hold a baby maintenance item thereon such as a towel, powder, or oil.

One other object of this invention is to provide a utility diaper structure including a disposable diaper assembly having a plurality of removable container assemblies thereon, each to hold a material therein in a sealed container member.

Still, one further object of this invention is to provide a utility diaper structure using a conventional, washable, diaper member and a plurality of packet assemblies which can be attached to the diaper member, each of the packet members holding a material therein to be used in baby maintenance.

Various other objects, advantages, and features of the invention will become apparent to those skilled in the art from the following discussion, taken in conjunction with the accompanying drawings, in which:

FIGURES OF THE INVENTION

Figure 1:
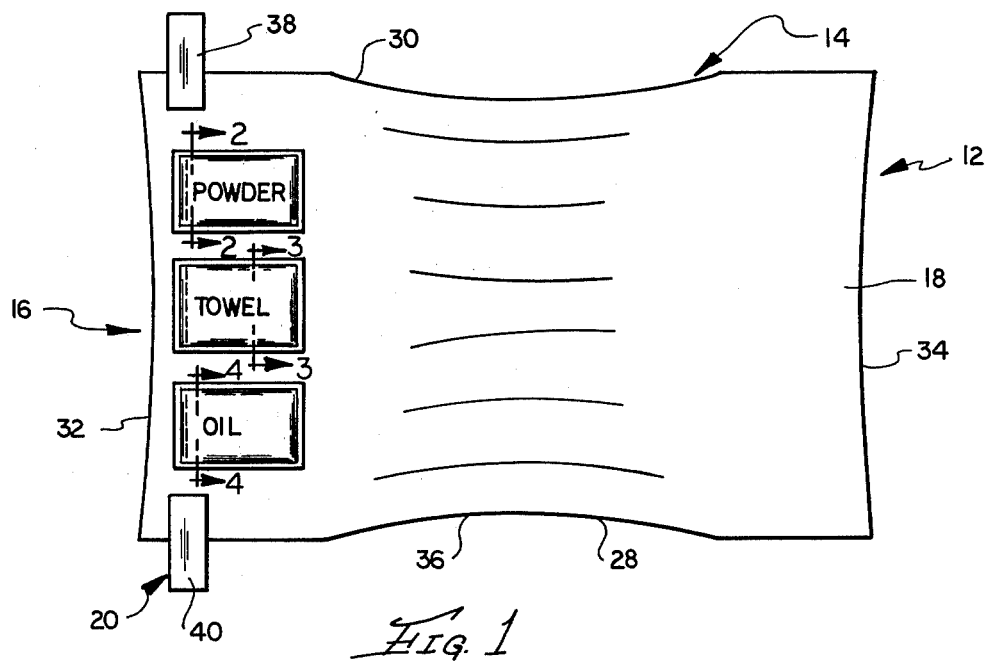
FIG. 1 is a top plan view of a utility diaper structure of this invention.

The following is a discussion and description of preferred specific embodiments of the new utility diaper structure of this invention, such being made with reference to the drawings, whereupon the same reference numerals are used to indicate the same or similar parts and/or structure. It is to be understood that such discussion and description is not to unduly limit the scope of the invention.

DESCRIPTION OF THE INVENTION

Referring to the drawings in detail and, in particular to FIG. 1, a utility diaper structure, indicated generally at 12, is shown in the open, unfolded condition. The diaper structure 12 includes a diaper assembly 14 having a container assembly 16 connected thereto.

The diaper structure 14 resembles a conventional re-washable or disposable type diaper having a main body member 18 with a connector assembly 20 secured thereto.

Figure 2:
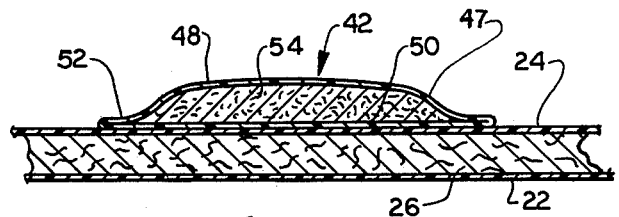
FIG. 2 is an enlarged sectional view taken along line 2—2 in FIG. 1.

The main body member 18 is of a generally rectangular shape and, as shown in FIG. 2, has a bottom layer 22, a top layer 24, and an absorbent material 26 mounted between the layers 22, 24. The main body member 18 is confined within sidewalls 28, 30 and endwalls 32, 34. Each sidewall 28,30 is formed with a curved section 36 to receive a portion of a baby's leg thereabout when in the usage position.

The connector assembly 20 includes left and right tab members 38, 40 secured adjacent the endwall 32 to the main body member 18. Each tab member 38, 40 is of generally rectangular shape and may have a snap member connected thereto or receive a safety pin for connection to the opposite portion of the main body member 18 in a conventional manner.

Figure 3:
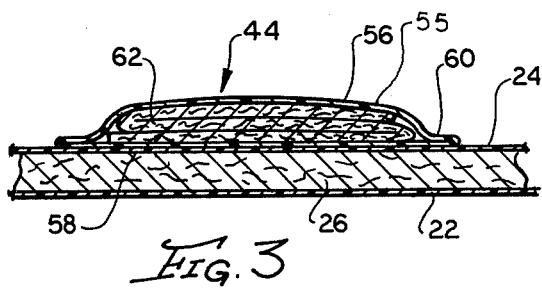
FIG. 3 is an enlarged sectional view taken along line 3—3 in FIG. 1.
Figure 4:
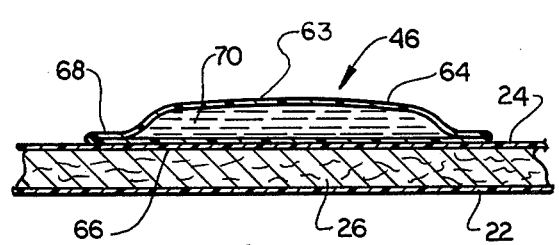
FIG. 4 is an enlarged sectional view taken along line 4—4 in FIG. 1.

As shown in FIGS. 2, 3, and 4, the container assemblies 16 include (1) a powder packet assembly 42; (2) a towel packet assembly 44; and (3) a baby oil packet assembly 46. The powder packet assembly 42 includes a container member 47 releasably connected as by an adhesive to the top layer 24 of the main body member 18.

The container member 47 includes a top wall 48 secured to a bottom wall 50 around outer peripheral edges 52 and having powder material 54 sealed therein. The top wall 48 can be peeled back to gain access to the powder material 54 as desired. The powder material 54 is of a baby powder type for normal usage on a baby to prevent chafing, etc.

As shown in FIG. 3, the towel packet assembly 44 includes a container member 55 which is connected by an adhesive material to the top layer 24 of the main body member 18. The container member 55 includes a top wall section 56 secured to a bottom wall section 58 around outer peripheral edge sections 60 and having a towel member 62 sealed therein. The top wall section 56 can be peeled back to gain ready access to the towel member 62 as desired. The towel member 62 may be of a dry type or of a dampened type depending on individual preference.

As shown in FIG. 4, the baby oil packet assembly 46 includes a container member 63 connected by an adhesive to the top layer 24 of the main body member 18.

The container member 63 includes a top wall portion 64 secured to a bottom wall portion 66 around outer peripheral edge portions 68 and having baby oil material 70 sealed therein. The top wall portion 64 can be peeled back to gain access to the baby oil material as desired.

USE AND OPERATION OF THE INVENTION

As best shown in FIG. 1, the utility diaper structure 12 is shown with the generally conventional diaper assembly 14 having one or more container assemblies 16 connected thereto. The container assemblies 16 are held to the main body member 18 of the diaper assembly 14 by a tacky type adhesive. This adhesive allows the container assemblies 16 to be readily removed from the main body member 18 and the subject adhesive remains only on the container assemblies 16 and not on the diaper assembly 14.

Although a plurality of three container assemblies 16 are shown, it is obvious that more or less may be used but the major elements of a powder, oil and maintenance towel are illustrated.

All of the container members 47, 55 and 63 are preferably constructed of a plastic material that provides a sanitary sealed container but can be provided with a tab or the like for easy opening thereof.

It is further noted that the container assemblies 16 may be provided individually so as to be connected by the adhesive to re-washable type diapers selectively by the baby's mother. Thus, the container assemblies 16 can be added when traveling so that the needed maintenance items will always be available.

The utility diaper structure is simple in construction, easy to use, and provides the much needed maintenance items for babies. The utility diaper structure eliminates the necessity of carrying along containers of baby oil, baby powder, and towels when traveling.

While the invention has been described in conjunction with preferred specific embodiments thereof, it will be understood that this description is intended to illustrate and not to limit the scope of the invention, which is defined by the following claims.

I claim:

1. A utility diaper structure adapted for use with human babies and the like, comprising:
   (a) a diaper assembly with a main body having a connector assembly adjacent outer end walls of said main body for securing about a waist area of a human baby;
   (b) a container assembly connected to said diaper assembly; and
   (c) said container assembly having a baby maintenance item sealed therein in a sanitary, sealed manner and releasably connected to said main body.

2. A utility diaper structure as described in claim 1, wherein:
   (a) said container assembly includes a top wall secured to a bottom wall about a sealed peripheral edge to contain said baby maintenance items therein; and
   (b) said container assembly releasably connected to an outer surface of said main body of said diaper assembly by an adhesive material.

3. A utility diaper structure as described in claim 1, wherein:
   (a) said baby maintenance item is baby powder material.

4. A utility diaper structure as described in claim 1, wherein:
   (a) said baby maintenance item is a towel member.

5. A utility diaper structure as described in claim 1, wherein:
   (a) said baby maintenance item is baby oil material.

6. A utility diaper structure as described in claim 1, including:
   (a) a plurality of said container assemblies are secured to an outer surface of said main body of said diaper assembly, each having a baby maintenance item therein.

7. A utility diaper structure as described in claim 6, wherein:
   (a) one of said container assemblies having a baby powder material sealed within a container member; and
   (b) said container member connected to said diaper assembly by an adhesive so as to be readily removed therefrom with all of said adhesive remaining on said container member and not on said outer surface of said main body.

8. A utility diaper structure as described in claim 6, wherein:
   (a) one of said container assemblies having a towel member sealed within a container member; and
   (b) said container member connected to said diaper assembly by an adhesive so as to be readily removed therefrom with all of said adhesive remaining on said container member and not on said outer surface of said main body.

9. A utility diaper structure as described in claim 6, wherein:
   (a) one of said container assemblies having a baby oil material sealed within a container member; and
   (b) said container member connected to said diaper assembly by an adhesive so as to be readily removed therefrom with all of said adhesive remaining on said container member and not on said outer surface of said main body.

* * * * *